(12) United States Patent
Proksa

(10) Patent No.: US 9,655,583 B2
(45) Date of Patent: May 23, 2017

(54) RADIOGRAPHIC IMAGING APPARATUS AND METHOD

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

(\*) Notice: Subject to any disclaimer, the term of this patent is extended or adjusted under 35 U.S.C. 154(b) by 0 days.

(21) Appl. No.: 15/334,345

(22) Filed: Oct. 26, 2016

(65) Prior Publication Data

US 2017/0042497 A1 Feb. 16, 2017

Related U.S. Application Data

(63) Continuation of application No. 14/434,209, filed as application No. PCT/IB2013/059092 on Oct. 3, 2013, now Pat. No. 9,504,438.

(Continued)

(51) Int. Cl.
*H01J 35/08* (2006.01)
*A61B 6/06* (2006.01)
(Continued)

(52) U.S. Cl.
CPC ............. *A61B 6/54* (2013.01); *A61B 6/4028* (2013.01); *A61B 6/4035* (2013.01); *A61B 6/42* (2013.01);
(Continued)

(58) Field of Classification Search
CPC .......... H01J 35/101; H01J 35/08; H01J 35/10; H01J 35/108; H01J 35/18; H01J 35/00;
(Continued)

(56) References Cited

U.S. PATENT DOCUMENTS 4,342,914 A \* 8/1982 Bjorkholm ............... A61B 6/06
378/113
4,344,012 A \* 8/1982 Hubner ................. H01J 35/108
313/311
(Continued)

FOREIGN PATENT DOCUMENTS

EP 1069439 1/2001
FR 2335854 7/1977
(Continued)

*Primary Examiner* — David A Vanore

(57) ABSTRACT

The present invention relates to a radiographic imaging apparatus and a corresponding radiographic imaging method. The proposed apparatus comprises an X-ray source and a photon counting X-ray detector. The X-ray source comprises a rotary X-ray anode having a number of radial slits and a target layer provided on a surface of said rotary X-ray anode in between said radial slits for emitting X-ray radiation when hit by said electron beam. The said photon counting X-ray detector comprises a persistent current sensing and correction unit for sensing a persistent output current in a blanking interval during which no X-ray radiation is emitted by said X-ray source and for using the sensed persistent output current to correct a detector signal in a subsequent measurement interval during which X-ray radiation is emitted by said X-ray source.

20 Claims, 4 Drawing Sheets

Related U.S. Application Data

(60) Provisional application No. 61/712,877, filed on Oct. 12, 2012.

(51) Int. Cl.
| | |
|---|---|
| *A61B 6/00* | (2006.01) |
| *G01T 1/24* | (2006.01) |
| *H01J 35/10* | (2006.01) |
| *G21K 1/04* | (2006.01) |

(52) U.S. Cl.
CPC ............. *A61B 6/4476* (2013.01); *G01T 1/24* (2013.01); *H01J 35/10* (2013.01); *G21K 1/043* (2013.01); *H01J 2235/086* (2013.01)

(58) Field of Classification Search
CPC .......... H01J 35/06; H01J 35/105; H01J 35/14; H01J 35/16; H01J 35/26; H01J 9/02; A31B 6/4021; A31B 6/502; A31B 6/4035; A31B 6/54; A31B 6/032; A31B 6/0407; A31B 6/0435; A31B 6/06; A31B 6/4028; A31B 6/42; A31B 6/4266; A31B 6/4441; A31B 6/4464; A31B 6/4476; A31B 6/483; A31B 6/585; A31B 6/586
USPC ....... 378/125, 144, 132, 133, 134, 146, 193, 378/37, 121, 143, 87, 113, 137, 140, 16, 378/160, 199, 57, 86
See application file for complete search history.

(56) References Cited

U.S. PATENT DOCUMENTS

| | | | | |
|---|---|---|---|---|
| 4,531,227 A | * | 7/1985 | Fukuhara | H01J 35/108 378/125 |
| 5,210,781 A | * | 5/1993 | Ono | H01J 35/101 378/125 |
| 5,222,114 A | * | 6/1993 | Kamata | G01N 23/046 378/125 |
| 6,118,850 A | | 9/2000 | Mayo | |
| 6,269,142 B1 | * | 7/2001 | Smith | G01N 23/20083 378/160 |
| 6,546,078 B2 | * | 4/2003 | Ide | H01J 35/101 378/125 |
| 6,907,110 B2 | | 6/2005 | Apel | |
| 7,286,645 B2 | * | 10/2007 | Freudenberger | A61B 6/4021 378/125 |
| 7,352,840 B1 | | 4/2008 | Nagarkar | |
| 7,796,737 B2 | * | 9/2010 | Allen | H01J 35/18 378/121 |
| 7,873,144 B2 | | 1/2011 | Luhta | |
| 7,933,382 B2 | * | 4/2011 | Hunt | H01J 35/101 378/132 |
| 8,094,782 B1 | * | 1/2012 | Annis | A61B 6/0435 378/37 |
| 8,363,787 B2 | * | 1/2013 | Lathrop | H01J 35/101 378/132 |
| 8,553,844 B2 | * | 10/2013 | Lewalter | H01J 35/108 378/125 |
| 9,099,279 B2 | * | 8/2015 | Rommel | H01J 35/10 |
| 9,504,438 B2 | * | 11/2016 | Proksa | G01T 1/24 |
| 9,538,979 B2 | * | 1/2017 | Behling | H01J 35/00 |
| 2004/0174959 A1 | | 9/2004 | Green | |
| 2004/0208288 A1 | * | 10/2004 | Lenz | B23H 7/108 378/121 |
| 2012/0128122 A1 | * | 5/2012 | Kautz | A61B 6/4021 378/16 |
| 2014/0126698 A1 | * | 5/2014 | Behling | H01J 35/10 378/62 |
| 2015/0265238 A1 | | 9/2015 | Proksa | |
| 2016/0133431 A1 | * | 5/2016 | Hunt | H01J 35/101 378/132 |

FOREIGN PATENT DOCUMENTS

| | | |
|---|---|---|
| WO | 2006080004 | 8/2006 |
| WO | 2007063479 | 6/2007 |
| WO | 2009007902 | 1/2009 |
| WO | 2012077023 | 6/2012 |
| WO | 2012095710 | 7/2012 |

* cited by examiner

RADIOGRAPHIC IMAGING APPARATUS AND METHOD

CROSS REFERENCE TO RELATED APPLICATIONS

This application is a continuation application of application Ser. No. 14/434,209, filed Apr. 8, 2015, published as US 2015-0265238 A1 on Sep. 24, 2015, which is a national filing of PCT application Serial No. PCT/IB2013/059092, filed Oct. 3, 2013, published as WO 2014/057400 A1 on Apr. 17, 2014, which is incorporated herein by reference, and which claims the benefit of U.S. provisional application Ser. No. 61/712,877 filed Oct. 12, 2012, which is incorporated herein by reference.

FIELD OF THE INVENTION

The present invention relates to a radiographic imaging apparatus comprising an X-ray source for projecting X-ray radiation into an examination region and a photon counting X-ray detector for receiving X-ray radiation after passing through said examination region and converting the received X-ray radiation into detector signals. Further, the present invention relates to a corresponding radiographic imaging method.

BACKGROUND OF THE INVENTION

A computed tomography (CT) scanner generally includes a rotating gantry rotatably mounted to a stationary gantry. The rotating gantry supports an X-ray tube and is configured to rotate around an examination region about a longitudinal axis. A detector array is located opposite the X-ray tube, across the examination region. The X-ray tube is configured to emit poly-energetic ionizing radiation that traverses the examination region (and a portion of an object or subject therein) and illuminates the detector array. The detector array includes a one or two dimensional array of detector pixels that detect the radiation and that generate signals indicative thereof. Each pixel is associated with a readout channel, which is used to convey a corresponding signal for further processing. A reconstructor reconstructs the processed signals, producing volumetric image data indicative of the examination region.

For spectral CT, the detector pixels have included direct conversion detector pixels. Generally, a direct conversion pixel includes a direct conversion material (e.g., cadmium telluride (CdTe), cadmium zinc telluride (CZT) etc.) disposed between a cathode and an anode, with a voltage applied across the cathode and the anode. X-ray photons illuminate the cathode, transferring energy to electrons in the direct conversion material, which creates electron/hole pairs, with the electrons drifting towards the anode. The anode, in response, produces the electrical signal output by the detector array. An amplifier amplifies the electrical signal, and a pulse shaper processes the amplified electrical signal and produces a pulse having a peak amplitude or height that is indicative of the energy of the detected radiation. An energy discriminator compares the height of the pulse with one or more energy thresholds. For each threshold, a counter counts the number of times the pulse height crosses the threshold. An energy-binner bins the counts in energy-ranges, thereby energy-resolving the detected radiation. The reconstructor reconstructs the binned signals using a spectral reconstruction algorithm.

Direct conversion material such as CdTe and CZT tends to produce a low frequency electrical current when irradiated with X-rays, which results in a baseline shift of the signals output by the detector pixels. Unfortunately, the baseline shift shifts the pulse output by the shaper, which can lead to erroneous binning of the detected radiation into incorrect energy bins as the discriminator thresholds remain static. There are two main components of this low frequency electrical current, namely dark current and persistent current. The dark current is a DC component that depends on the detector material and the bias voltage and usually does not change during an acquisition interval. This component can simply be corrected with a static bias compensation, which injects the same amount of current with the opposite sign to the input of the amplifier. The persistent current (PC) is caused by trapping (in the direct conversion material) of holes of the electron-hole pairs. Because of the positive potential of the trapped charges, electrons are injected into the bulk material and move to the anode instead of recombining with the holes. The resulting slowly varying current can be very strong and can exceed the photo current (the amount of charge directly generated by photons) by two orders of magnitude. This persistent current causes significant signal degradation and may generate unacceptable image artefacts if left uncorrected. Unfortunately, the persistent current dynamically changes and cannot simply be compensated with a static signal of the opposite sign like the dark current.

SUMMARY OF THE INVENTION

It is an object of the present invention to provide a radiographic imaging apparatus and method that provide a simple and robust way of persistent current compensation.

In a first aspect of the present invention a radiographic imaging apparatus is presented comprising an X-ray source for projecting X-ray radiation into an examination region and a photon counting X-ray detector for receiving X-ray radiation after passing through said examination region and converting the received X-ray radiation into detector signals, wherein said X-ray source comprises
  a cathode for emitting an electron beam,
  a rotary X-ray anode having a number of radial slits and
    a target layer provided on a surface of said rotary X-ray anode in between said radial slits for emitting X-ray radiation when hit by said electron beam, and
  a drive unit for rotating said X-ray anode,
and
wherein said photon counting X-ray detector comprises
  a direct conversion X-ray detection unit for receiving the X-ray radiation and outputting an electrical signal,
  a photon counting unit for generating, from said electrical signal, said detector signal representing the number of photons of the received X-ray radiation, and
  a persistent current sensing and correction unit for sensing a persistent output current in a blanking interval during which no X-ray radiation is emitted by said X-ray source and for using the sensed persistent output current to correct a detector signal generated by said photon counting unit in a subsequent measurement interval during which X-ray radiation is emitted by said X-ray source.

In a further aspect of the present invention a radiographic imaging method is presented comprising
  projecting X-ray radiation into an examination region by use of an X-ray source comprising a cathode for emitting an electron beam, a rotary X-ray anode having a number of radial slits and a target layer provided on a surface of said rotary X-ray anode in between said radial slits for emitting X-ray radiation when hit by said electron beam, and a drive unit for rotating said X-ray anode, receiving X-ray radiation after passing through said examination region by use of a direct conversion X-ray detection unit, outputting an electrical signal from said direct conversion X-ray detection unit, converting the electrical signal into a detector signal representing the number of photons of the received X-ray radiation, sensing the persistent output current of the photon counting unit in a blanking interval during which no X-ray radiation is emitted by said X-ray source, and using the sensed persistent output current to correct a detector signal generated by said photon counting unit in a subsequent measurement interval during which X-ray radiation is emitted by said X-ray source.

Preferred embodiments of the invention are defined in the dependent claims. It shall be understood that the claimed method has similar and/or identical preferred embodiments as the claimed system and as defined in the dependent claims.

A very powerful correction scheme for compensation of persistent current is to periodically blank the X-ray beam during the acquisition, sense the device current during these intervals and use the obtained result for a DC correction of the successive measurement interval until the next blanking and PC sensing is performed. For periodically blanking the X-ray beam a slit anode is used. Some ultra high power X-ray tubes for CT imaging have such radial slits in the rotating anode to reduce the thermo mechanical stress of the anode. Whenever such a slit passes the electron beam, the output X-ray flux is temporarily reduced. Such a slit anode is e.g. described in U.S. Pat. No. 4,531,227.

According to the present invention the X-ray blanking by use of a slit anode (also called slotted anode) is combined with the PC sensing intervals of a photon counting detector. Further, the persistent output current of the photon counting unit of the photon counting detector is sensed in a blanking interval during which no X-ray radiation is emitted. The sensed persistent output current is then used to correct a detector signal generated by said photon counting unit in a subsequent measurement interval during which X-ray radiation is emitted by said X-ray source. This provides for the desired simple and efficient way of persistent current compensation.

The anode of the X-ray tube is optimized for this purpose. In an embodiment the width of the radial slits of the rotary anode is configured such that during a blanking interval the persistent output current can be completely sensed by said persistent current sensing and correction unit. Further, in an embodiment the radial slits of the rotary anode have a minimum slit width of $FS+(R \times \Omega \times T)$, wherein FS is the focal spot size on the anode, R is the radius of the focal track on the rotary anode, $\Omega$ is the angular speed of the rotary anode and T is the minimum time required for completely sensing the persistent output current by said persistent current sensing and correction unit. Herein, preferably, R is in the range from 5 cm to 35 cm, $\Omega$ is in the range from $2\pi \times 50$ Hz to $2\pi \times 400$ Hz, and T is in the range from 0.1 µsec to 100 µsec, and further said the angular width of a slit is in the range from 0.5 mm to 3 mm. In this way a practically useful implementation is provided.

In a simply implementable embodiment said persistent current sensing and correction unit comprises an amplifier coupled between the output of said direct conversion X-ray detection unit and the input of said photon counting unit for amplifying said electrical signal, and a sample and hold unit for receiving said amplified electrical signal and generating, during the blanking interval, a compensation signal coupled to the output of said direct conversion X-ray detection unit for dynamically adjusting electrical signal to compensate the persistent output current. The sample and hold unit provides a PC compensation current to the input of the detection unit. During X-ray blanking, the sample and hold unit dynamically adjusts the output current to compensate the PC current. After the blanking interval, the compensation current is frozen and kept constant for the successive measurement interval.

Thus, said sample and hold unit preferably comprises a switch for enabling a dynamic adjustment of the electrical signal during a blanking interval by use of the dynamically generated compensation signal and for keeping the compensation signal constant during a subsequent measurement interval.

There are different embodiments for controlling said switch. In one embodiment the switch is advantageously controlled by a blanking signal to be synchronously with the blanking interval switched on and off.

In another embodiment said switch is controlled by a blanking signal to be asynchronously with the measurement intervals of the photon counting X-ray detector and wherein a reference measurement is used to correct for X-ray flux variation caused by flux blanking. This embodiment does not require synchronization of the rotating tube anode and the measurement intervals, but requires reference measurements to compensate for flux variation caused by the X-ray blanking.

In still another embodiment said switch is controlled by a blanking signal to be synchronously with the measurement intervals of the photon counting X-ray detector and between two successive measurement intervals. This embodiment has the advantage to keep the measurement intervals constant. This avoids the need to compensate varying measurement intervals.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
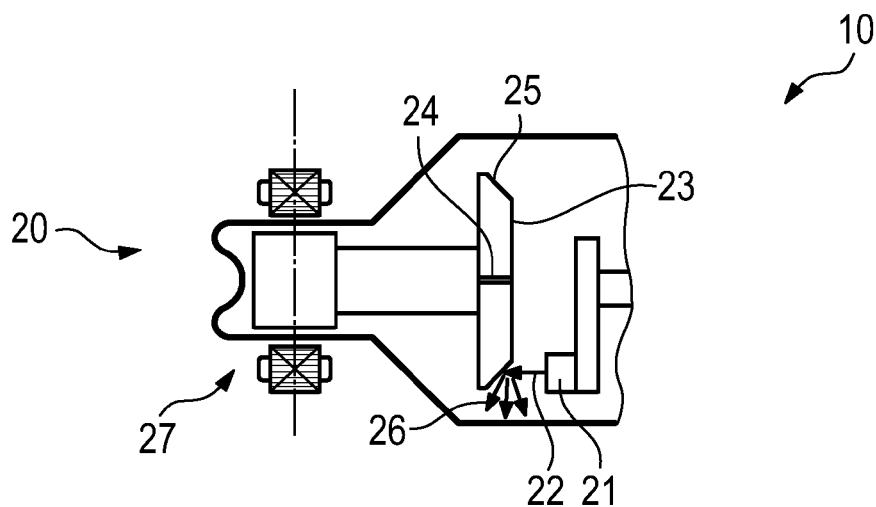
FIG. 1 shows a first embodiment of a proposed radiographic imaging apparatus.
Figure 1:
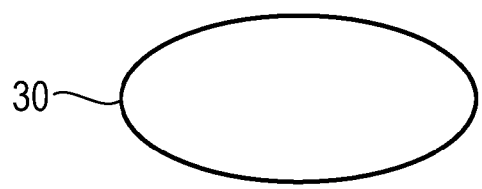
Figure 1:
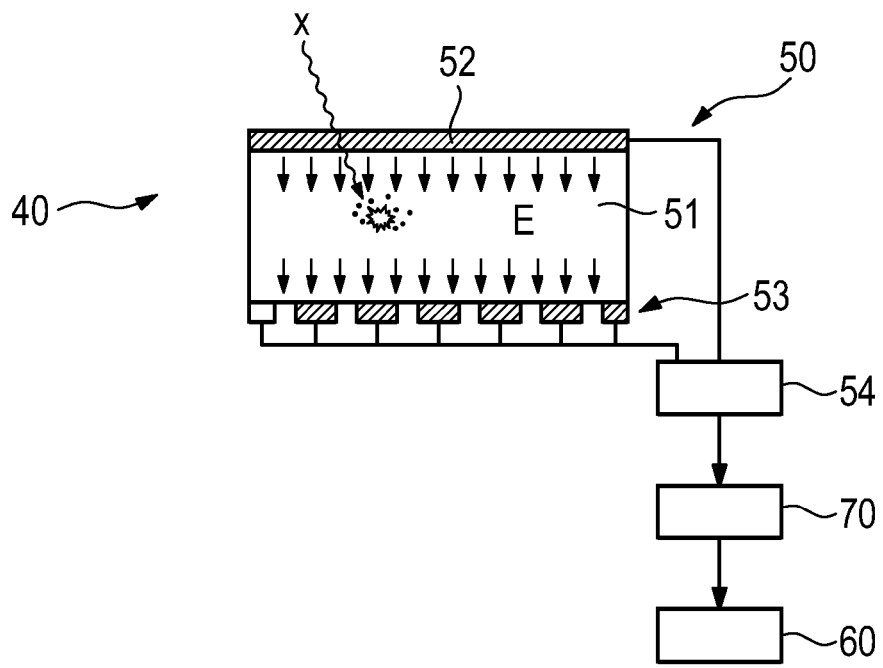

FIG. 1 shows a first embodiment of a proposed radiographic imaging apparatus 10. It comprises an X-ray source 20 for projecting X-ray radiation into an examination region 30 and a photon counting X-ray detector 40 for receiving X-ray radiation after passing through said examination region 30 and converting the received X-ray radiation into detector signals. In the examination region an object of examination, e.g. a patient, may be placed, e.g. lying on a patient table as generally known in the art.

The X-ray source 20 comprises a cathode 21 for emitting an electron beam 22 and a rotary X-ray anode 23 having a number of radial slits 24 and a target layer 25 provided on a surface of said rotary X-ray anode 23 in between said radial slits 24 for emitting X-ray radiation 26 when hit by said electron beam 22. A drive unit 27, e.g. formed as an electric motor comprising a rotor and a stator body, is provided for rotating said X-ray anode 23.

Figure 2:
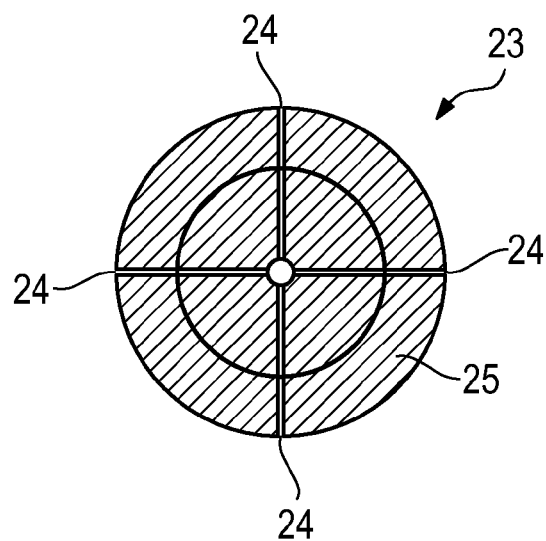
FIG. 2 shows a top view onto a rotary X-ray anode having radial slits.

A top view on a rotary X-ray anode 23 having—in this exemplary embodiment—four radial slits 24 between the target material 25 is depicted in FIG. 2. A rotary X-ray anode having such slits is generally known in the art, e.g. from U.S. Pat. No. 4,531,227.

The photon counting X-ray detector 40 comprises a direct conversion X-ray detection unit 50 for receiving the X-ray radiation and outputting an electrical signal, a photon counting unit 60 for generating, from said electrical signal, said detector signal representing the number of photons of the received X-ray radiation, and a persistent current sensing and correction unit 70 coupled between said X-ray detection unit 50 and said photon counting unit 60.

Energy resolving detectors for X-ray and gamma radiation based on direct converter materials, as for example CdTe or CZT, can efficiently measure photon energies. The direct conversion X-ray detection unit 50 comprises a "converter element" 51, i.e. a block of semiconductor material, located between a cathode 52 and an array of anodes 53. A (high) voltage is applied to these electrodes by a readout unit 54. An incident photon X creates a number of electron/hole pairs. Thereafter, the electrons drift to the array of anode pixels 53 at the "bottom" side, while holes drift to the cathode 52. It is important to note, that already during the drift of the charge carriers a current is induced into the pixel anodes due to capacitive coupling. The currents in the pixel anodes are read out by the readout unit 54, which output electrical signals for subsequent evaluation. Such direct conversion X-ray detection unit is generally known in the art, e.g. from WO 2012/077023 A2.

The persistent current sensing and correction unit 70 senses the persistent output current of the direct conversion X-ray detection unit 50 in a blanking interval during which no X-ray radiation is emitted by said X-ray source and uses the sensed persistent output current to correct a detector signal generated by said photon counting unit 60 in a subsequent measurement interval during which X-ray radiation is emitted by said X-ray source 20.

The anode 23 of the X-ray tube 20 is preferably be optimized for this purpose. In an embodiment the anode 23 has about eight slits and a rotation frequency of about 200 Hz. The resulting blanking period is about 600 μsec which is close to a typical integration interval of a CT scanner. The slit width is preferably specified such that the X-ray flux is entirely blanked for a time period that matches the requirements of the PC sampling electronics, in particular the persistent current sensing and correction unit 70. In an embodiment an X-ray tube controller (not shown) should provide an electrical signal to indicate a blanking interval related to a slit 24 passing the electron beam 22.

Figure 3:
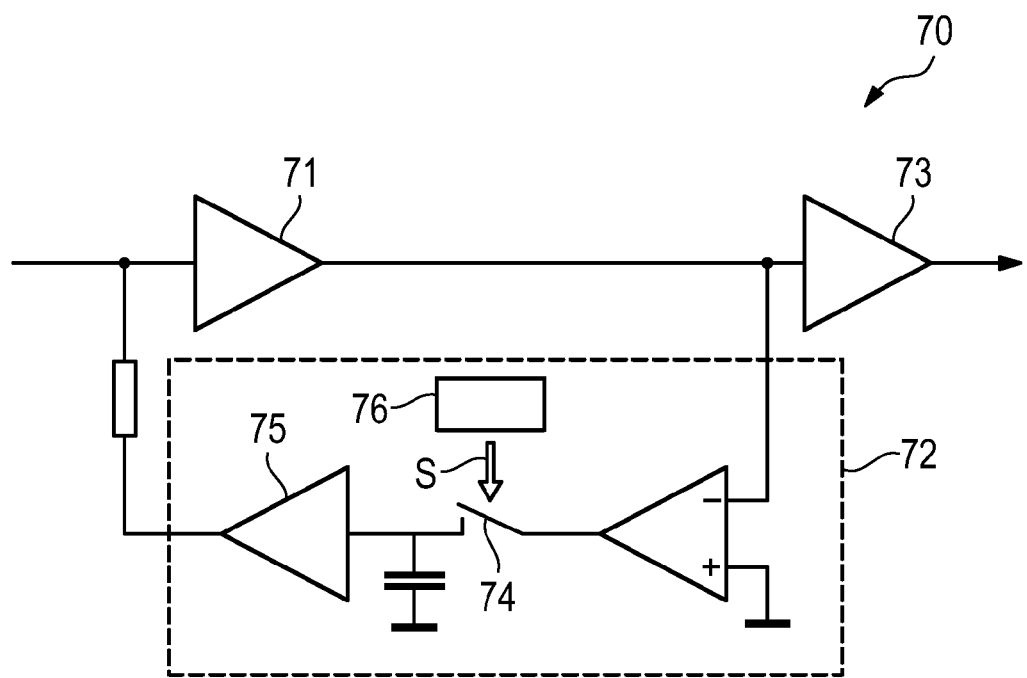
FIG. 3 shows an embodiment of a proposed persistent current sensing and correction unit.

Preferably, the radial slits 24 of the rotary anode 23 have a minimum slit width of $FS+(R\times\Omega\times T)$, wherein FS is the focal spot size on the anode 23, R is the radius of the focal track on the rotary anode 23, $\Omega$ is the angular speed of the rotary anode 23 and T is the minimum time required for completely sensing the persistent output current by said persistent current sensing and correction unit 70. Typically, R is in the range from 5 cm to 35 cm, $\Omega$ is in the range from $2\pi\times50$ Hz to $2\pi\times400$ Hz, and T is in the range from 0.1 μsec to 100 μsec. The angular width of a slit is preferably in the range from 0.5 mm to 3 mm FIG. 3 shows an embodiment of a proposed persistent current sensing and correction unit 70. It comprises an amplifier 71 coupled between the output of said direct conversion X-ray detection unit 50 and the input of said photon counting unit 60 for amplifying said electrical signal, and a sample and hold unit 72 for receiving said amplified electrical signal and generating, during the blanking interval, a compensation signal coupled to the output of said direct conversion X-ray detection unit 50 for dynamically adjusting the electrical signal to compensate the persistent output current. Preferably, an additional pulse shaper 73 is provided at the output of the persistent current sensing and correction unit 70.

In the embodiment shown in FIG. 3 the sample and hold unit 72 comprises a switch 74 for enabling a dynamic adjustment of the electrical signal during a blanking interval (e.g. controlled by an X-ray blanking signal S provided from a controller 76) by use of the dynamically generated compensation signal and for keeping the compensation signal constant during a subsequent measurement interval. For this purpose a buffer amplifier 75 is provided at the output of the switch 74. The two amplifiers in the sample-and-hold feedback path are mainly used to decouple the switch and hold-capacitor from the pre amplifier, and further, to avoid a discharge of the hold-capacitor by the compensation current.

Thus, the sample and hold unit 72 thus provides a PC compensation current to the input of the photon counting unit 60. During X-ray blanking, the sample and hold unit 72 will dynamically adjust the output current to compensate the PC current (switch 74 is closed). After the blanking interval, the compensation current is frozen and kept constant for the successive measurement interval (switch 74 is open).

In a preferred embodiment the blanking intervals are synchronously with the detector acquisition intervals (or with the anode rotation). In another preferred embodiment the blanking intervals may be asynchronously to the detector acquisition intervals. Often, CT scanners have a reference detector to monitor the output flux of the tube for each acquisition period. The acquired data are than used to correct for flux variation. Such a scheme may be used in this embodiment, which then automatically compensates for integral flux changes caused by the blanking intervals. Alternatively the anode rotation may be synchronized to the acquisition frequency or vice versa.

Figure 4:
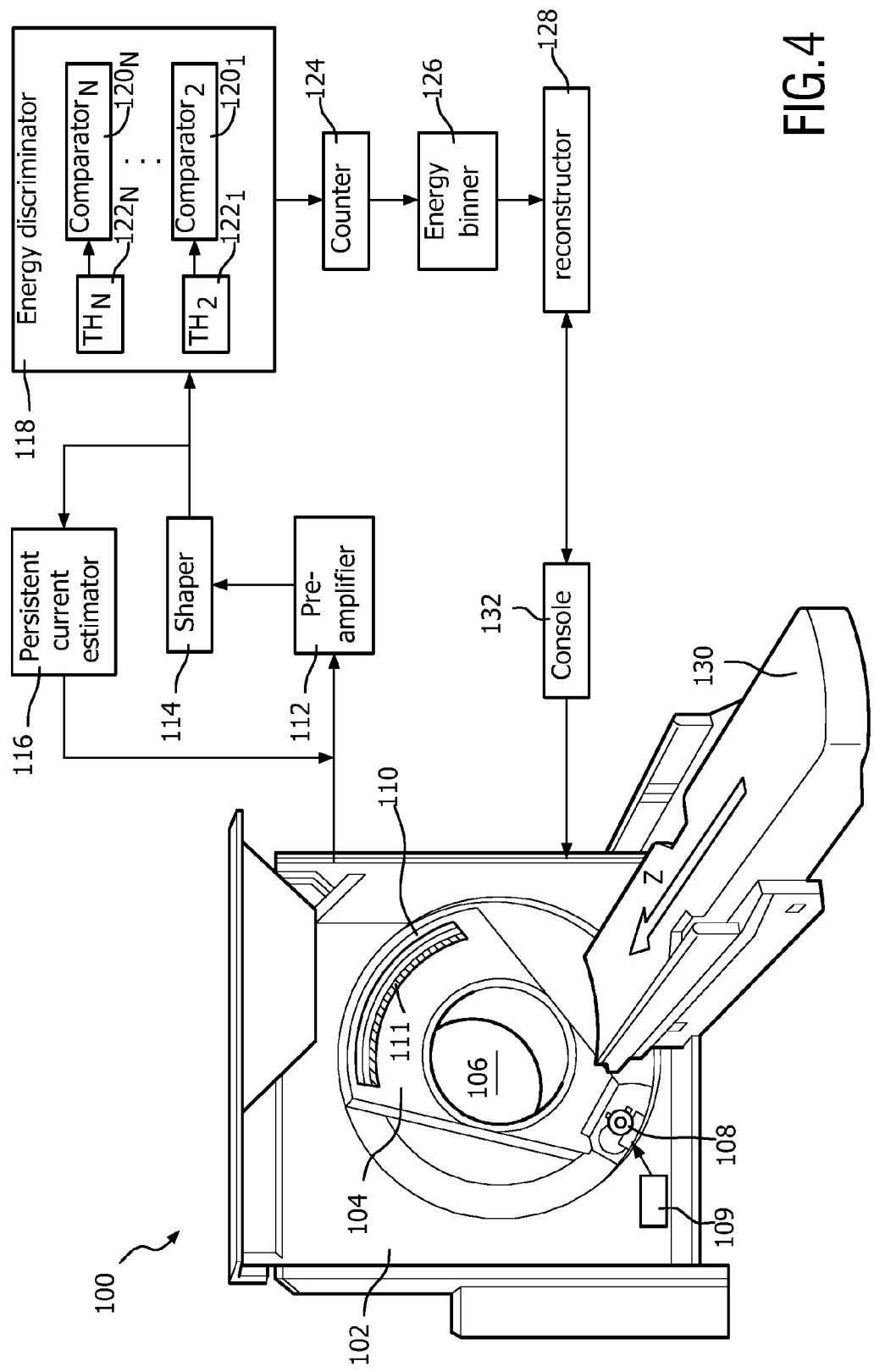
FIG. 4 shows a second embodiment of a proposed radiographic imaging apparatus.

FIG. 4 shows a second embodiment of a proposed radiographic imaging apparatus 100 which is implemented as a computed tomography (CT) scanner. The imaging apparatus 100 includes a stationary gantry 102 and a rotating gantry 104, which is rotatably supported by the stationary gantry 102. The rotating gantry 104 rotates around an examination region 106 about a z-axis. A radiation source 108, such as an X-ray tube, is supported by and rotates with the rotating gantry 104 around the examination region 106 about the z-axis. The source 108 emits radiation that traverses the examination region 106. An optional radiation controller 109 transitions a state of radiation emission between a first state in which radiation traverses the examination region 106 and a second state in which radiation does not traverse the examination region 106. This may include turning the source 108 "on"/"off," inserting/removing a filter from the path of radiation, applying/removing a grid voltage to a switching grid of the source 108 to inhibit/allow electrons to flow from the cathode to the anode of the source 108, etc.

A radiation sensitive detector array 110 subtends an angular arc across the examination region 106 opposite the radiation source 108. The detector array 110 detects radiation that traverses the examination region 106 and generates an electrical (e.g., a voltage or current) signal indicative thereof. The illustrated detector array 110 includes one or more rows of photon counting detector pixels 111 such as direct conversion detector pixels including a direct conversion crystal or material. For each of the detector pixels 111, an optional pre-amplifier 112 amplifies the electrical signal, and a pulse shaper 114 receives the electrical signal or amplified signal and generates a pulse (e.g., voltage or current) having a peak height or amplitude that is indicative of the energy level of the corresponding incident detected radiation.

A persistent current estimator 116 (that corresponds to the persistent current sensing and correction unit 70) estimates, for each detector pixel 111, a value of the persistent current at the output of the corresponding shaper 114 and generates a persistent current compensation signal for each detector pixel 111. For a detector pixel 111, the persistent current sensing and correction unit 116 feeds or injects the compensation signal back to the input of the corresponding pre-amplifier 112, which substantially cancels the persistent current of that detector pixel 111 at the input of the pre-amplifier 112. This may substantially mitigate the baseline shift at the output of the shaper 114 of a detector pixel 111 due to the persistent current of that detector pixel 111.

An energy-discriminator 118 energy-discriminates the pulse output by the shaper 114 for each detector pixel 111. The illustrated energy-discriminator 118 includes a set of comparators $120_1, \ldots, 120_N$ (collectively referred to herein as comparators 120) and a corresponding set of predetermined energy thresholds (TH) $122_1, \ldots 122_N$ (collectively referred to herein as energy thresholds 122), where N is an integer equal to or greater than one. Each of the comparators 120 compares the height of an incoming pulse with its respective one of the thresholds 122 and generates an output signal that indicates whether the peak height exceeded that threshold 122.

A counter 124 (that corresponds to the photon counting unit 60) counts, for each of the comparators 120, when an individual threshold is exceeded by a peak of a pulse, for each of the plurality of pulses. An energy-binner 126 bins the counts into energy ranges based on a relationship between the threshold levels and the energy of incoming radiation, thereby energy-resolving the detected radiation. A reconstructor 128 reconstructs the energy-binned signals. The reconstructor 128 can employ a spectral and/or a non-spectral reconstruction algorithm to reconstruct the energy-binned signals.

A subject support 130, such as a couch, supports an object or subject in the examination region 106. The subject support 130 can be used to vertically and/or horizontally position the subject or object relative to the imaging system 100 before, during, and/or after scanning. A general purpose computing system serves as an operator console 132 and includes an output device such as a display and an input device such as a keyboard, mouse, and/or the like. Software resident on the console 132 allows the operator to interact and/or operate the imaging system 100. Such interaction may include selecting an imaging protocol with or without grid switching, initiating scanning, etc.

For further details of the function of the persistent current estimator and the way of compensating persistent current reference is made to the description of the first embodiment which basically holds for the second embodiment as well.

Figure 5:
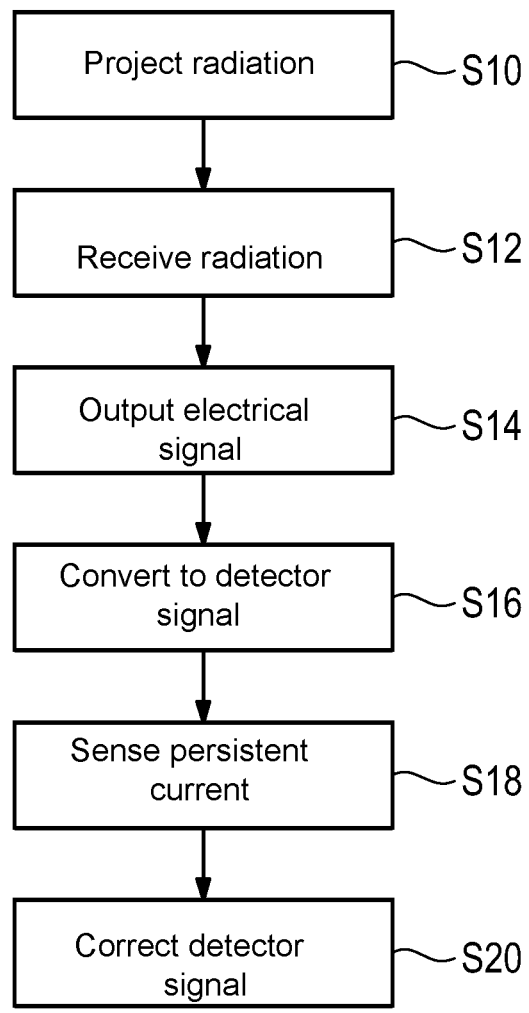
FIG. 5 shows a flowchart illustrating an embodiment of the proposed radiographic imaging method.

FIG. 5 shows a flowchart of an embodiment of the proposed radiographic imaging method. Said method comprises the steps of projecting (S10) X-ray radiation into an examination region by use of an X-ray source comprising a cathode for emitting an electron beam, a rotary X-ray anode having a number of radial slits and a target layer provided on a surface of said rotary X-ray anode in between said radial slits for emitting X-ray radiation when hit by said electron beam, and a drive unit for rotating said X-ray anode, receiving (S12) X-ray radiation after passing through said examination region by use of a direct conversion X-ray detection unit, outputting (S14) an electrical signal from said direct conversion X-ray detection unit, converting (S16) the electrical signal into a detector signal representing the number of photons of the received X-ray radiation, sensing (S18) the persistent output current of the photon counting unit in a blanking interval during which no X-ray radiation is emitted by said X-ray source, and using (S20) the sensed persistent output current to correct a detector signal generated by said photon counting unit in a subsequent measurement interval during which X-ray radiation is emitted by said X-ray source.

Further embodiments and variations of the proposed radiographic imaging method are possible corresponding to the embodiments and variations of the radiographic imaging device described above.

In summary, the present invention provides a simple device and method for periodically X-ray flux pulsing for CT imaging to enable dynamic calibration of the persistent current in CZT photon counting detectors with ohmic contacts.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:
1. An imaging apparatus, comprising:
a radiation source, including:
 a cathode configured to emit an electron beam;
 an anode, including:
  a plurality of radial slits; and
  a target layer disposed on a surface of the anode between the radial slits, wherein the target layer is configured to emit X-ray radiation in response to receiving the electron beam; and a drive unit configured to rotate the X-ray anode during scanning such that during a first time interval the electron beam passes through the plurality of radial slits and during a subsequent time interval the target layer receives the electron beam and emits the X-ray radiation; and a radiation detector configured to generate a first electrical signal during the first time interval and detect the emitted X-ray radiation and generate a subsequent electrical signal indicative thereof during the subsequent time interval.

2. The imaging apparatus of claim 1, further comprising:
first circuitry configured to generate a first detector signal indicative of a first number of photons of the received X-ray radiation during the first time interval from the first electrical signal.

3. The imaging apparatus of claim 2, further comprising:
second circuitry configured to sense a persistent electrical current in the first signal.

4. The imaging apparatus of claim 3, wherein the first circuitry is further configured to generate a subsequent detector signal indicative of a subsequent number of photons during the subsequent time interval from the subsequent electrical signal.

5. The imaging apparatus of claim 4, wherein the second circuitry is further configured to correct, based on the persistent electrical current, the subsequent detector signal.

6. The imaging apparatus of claim 5, further comprising:
third circuitry which energy-discriminates and bins the corrected subsequent detector signal; and
a reconstructor that reconstructs the energy-binned signal to produce an image.

7. The imaging apparatus of claim 1, wherein a slit of the plurality of radial slits includes a width, which is equal to $FS+(R \times \Omega \times T)$, wherein the parameter FS is a focal spot size on the anode, the parameter R is a radius of a focal track on the anode, the parameter $\Omega$ is an angular speed of the anode, and the parameter T is a minimum time required to sense the persistent electrical current.

8. The imaging apparatus of claim 7, wherein the parameter R is in a range from 5 centimeters to 35 centimeters, the parameter $\Omega$ is in a range from $2\pi \times 50$ Hertz to $2\pi \times 400$ Hertz, and the parameter T is in a range from 0.1 micro-seconds to 100 micro-seconds.

9. The imaging apparatus of claim 7, wherein the width is in a range from 0.5 millimeter to 3 millimeters.

10. The imaging apparatus of claim 5, wherein the second circuitry comprises:
sample and hold circuitry configured to receive the first detector signal and generate a persistent current compensation signal based on the persistent electrical current, and wherein the second circuitry corrects the subsequent electrical signal with the persistent current compensation signal.

11. The imaging apparatus of claim 10, wherein the sample and hold circuitry comprises:
a switch configured to enable dynamic adjustment of the subsequent electrical signal with the persistent current compensation signal.

12. The imaging apparatus of claim 11, wherein the switch is controlled to switch synchronously with the first and subsequent time intervals.

13. The imaging apparatus of claim 11, wherein the switch is controlled to switch asynchronously with the subsequent time interval, where a reference signal corrects for a variation in x-ray flux.

14. The imaging apparatus of claim 11, wherein the subsequent time interval is a measurement interval, and the switch is controlled to switch synchronously with the first time interval.

15. A method, comprising:
rotating a slotted anode of a radiation source, wherein the slotted anode includes a plurality of radial slits with a target layer disposed on a surface of the anode in between the plurality of radial slits;
emitting, concurrently with rotating the slotted anode, an electron beam with a cathode of the radiation source;
wherein the radiation source emits an X-ray beam during periods in which the electron beam is received by the target layer and does not emit the X-ray beam during periods in which the electron beam passes through the plurality of radial slits;
detecting, with a radiation detector, the emitted X-ray radiation; and
generating a first electrical signal indicative thereof during the periods in which the electron beam is received by the target layer and generating a second electrical signal during the periods in which the electron beam passes through the plurality of radial slits.

16. The method of claim 15, further comprising:
sensing a persistent electrical current of the radiation detector from the second electrical signal.

17. The method of claim 16, further comprising:
correcting the first electrical signal with the sensed persistent electrical current.

18. A non-transitory computer readable medium encoded with computer executable instruction which when executed by a processor cause the processor to:
rotate a slotted anode of a radiation source, wherein the slotted anode includes a plurality of radial slits with a target layer disposed on a surface of the anode in between the plurality of radial slits;
emit, concurrently with rotating the slotted anode, an electron beam with a cathode of the radiation source;
wherein the radiation source emits an X-ray beam during periods in which the electron beam is received by the target layer and does not emit the X-ray beam during periods in which the electron beam passes through the plurality of radial slits;
detect, with a radiation detector, the emitted X-ray radiation; and
generate a first electrical signal indicative thereof during the periods in which the electron beam is received by the target layer and generate a second electrical signal during the periods in which the electron beam passes through the plurality of radial slits.

19. The non-transitory computer readable medium of claim 18, wherein executing the computer executable instructions further causes the processor to:
rotate the slotted anode synchronously with data acquisition intervals.

20. The non-transitory computer readable medium of claim 18, wherein executing the computer executable instructions further causes the processor to:
rotate the slotted anode asynchronously with data acquisition intervals.

* * * * *